United States Patent
Krauss

(10) Patent No.: US 10,510,166 B2
(45) Date of Patent: Dec. 17, 2019

(54) REDUCING THE NUMBER OF SPECTRAL CHANNELS IN MULTI-ENERGY CT IMAGING

(71) Applicant: Siemens Healthcare GmbH, Erlangen (DE)

(72) Inventor: Bernhard Krauss, Burgthann (DE)

(73) Assignee: SIEMENS HEALTHCARE GMBH, Erlangen (DE)

(*) Notice: Subject to any disclaimer, the term of this patent is extended or adjusted under 35 U.S.C. 154(b) by 120 days.

(21) Appl. No.: 15/841,754

(22) Filed: Dec. 14, 2017

(65) Prior Publication Data
US 2018/0189986 A1 Jul. 5, 2018

(30) Foreign Application Priority Data
Jan. 3, 2017 (DE) .................. 10 2017 200 032

(51) Int. Cl.
G06T 11/00 (2006.01)
A61B 6/03 (2006.01)
A61B 6/00 (2006.01)
G06T 7/00 (2017.01)

(52) U.S. Cl.
CPC ............ *G06T 11/006* (2013.01); *A61B 6/032* (2013.01); *A61B 6/482* (2013.01); *A61B 6/5205* (2013.01); *A61B 6/5211* (2013.01); *A61B 6/5258* (2013.01); *G06T 7/0012* (2013.01);
(Continued)

(58) Field of Classification Search
USPC .......................................... 382/128, 131–132
See application file for complete search history.

(56) References Cited

U.S. PATENT DOCUMENTS 7,801,265 B2 * 9/2010 Yu .......................... A61B 6/032
378/4
8,031,831 B2 * 10/2011 Zou ........................ A61B 6/032
378/108
(Continued)

FOREIGN PATENT DOCUMENTS

DE 102011083727 A1 4/2013

OTHER PUBLICATIONS

Alvarez, Robert E. et al.: Energy-selective Reconstructions in X-ray Computerized Tomography, Phys. Med. Biol., 1976, vol. 21, No. 5, pp. 733-744.
(Continued)

*Primary Examiner* — Ishrat I Sherali
(74) *Attorney, Agent, or Firm* — Harness, Dickey & Pierce, P.L.C.

(57) ABSTRACT

A method for the reconstruction of image data based upon a plurality of multi-energy projection measurement data sets of a field of examination of an object under examination is described. In an embodiment of the method, a plurality of projection measurement data sets, produced via multi-energy CT imaging using differing X-ray energy spectra of the field of examination of the object under examination, are captured. In addition, a reduced number of image data sets are produced based upon the plurality of projection measurement data sets by applying a basic material decomposition and an image mix. An image data reconstruction facility is also described. Furthermore a computed tomography system is described.

19 Claims, 4 Drawing Sheets

(52) U.S. Cl.
CPC ............... *G06T 2207/10081* (2013.01); *G06T 2211/408* (2013.01)

(56) References Cited

U.S. PATENT DOCUMENTS

| | | | |
|---|---|---|---|
| 8,160,206 B2* | 4/2012 | Wu | A61B 6/032 378/4 |
| 8,194,961 B2* | 6/2012 | Zou | G06T 11/005 378/5 |
| 9,070,181 B2* | 6/2015 | Wu | G06T 7/0012 |
| 9,870,628 B2* | 1/2018 | Gronberg | G01N 23/046 |
| 2011/0150183 A1 | 6/2011 | Benson et al. | |
| 2012/0039440 A1 | 2/2012 | Fan et al. | |
| 2013/0083989 A1 | 4/2013 | Flohr et al. | |
| 2015/0363947 A1* | 12/2015 | Rigie | G06T 11/005 382/131 |
| 2016/0106386 A1 | 4/2016 | Fan et al. | |

OTHER PUBLICATIONS

Faby Sebastian et al: "Performance of today's dual energy CT and future multi energy CT in virtual non-contrast imaging and in iodine quantification: A simulation study"; Medical Physics vol. 42 No. 7; pp. 4349-4366; Jul. 2015.; 2015.
Riederer S. J. and Mistretta C. A., "Selective iodine imaging using K-edge energies in computerized x-ray tomography", Medical Physics, vol. 4, No. 6, Nov./Dec. 1977, pp. 474-481.
Yu Lifeng et al: "Virtual monochromatic imaging in dual-source dual-energy CT: radiation dose and image quality"; Med. Phys. Dec. 2011; pp. 6371-6379; 2011.
German Office Action #102017200032.5 dated Sep. 18, 2017.

* cited by examiner

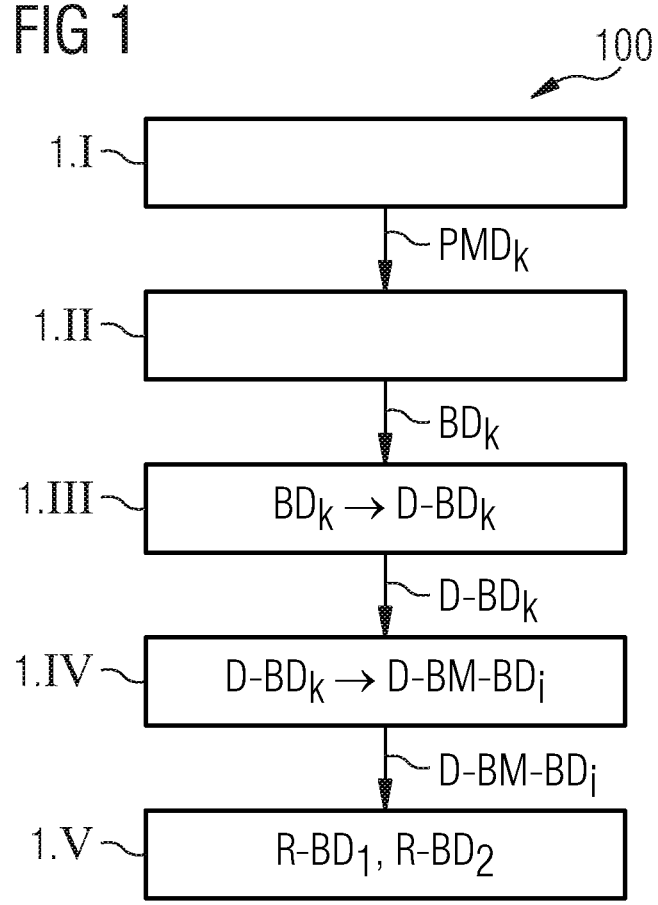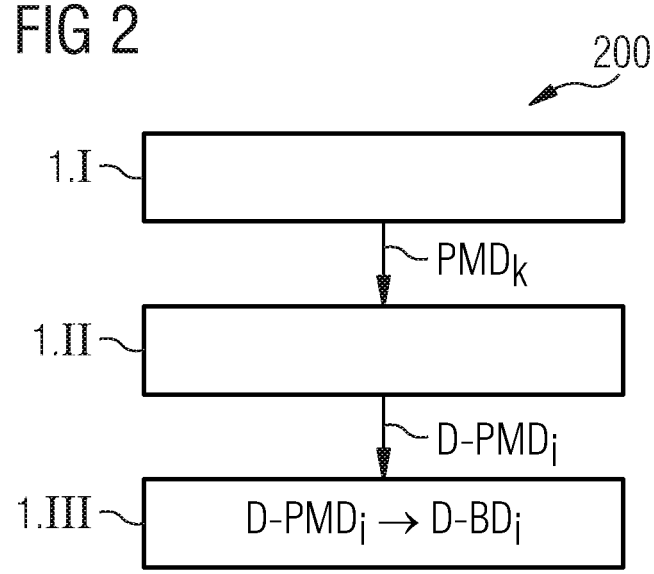

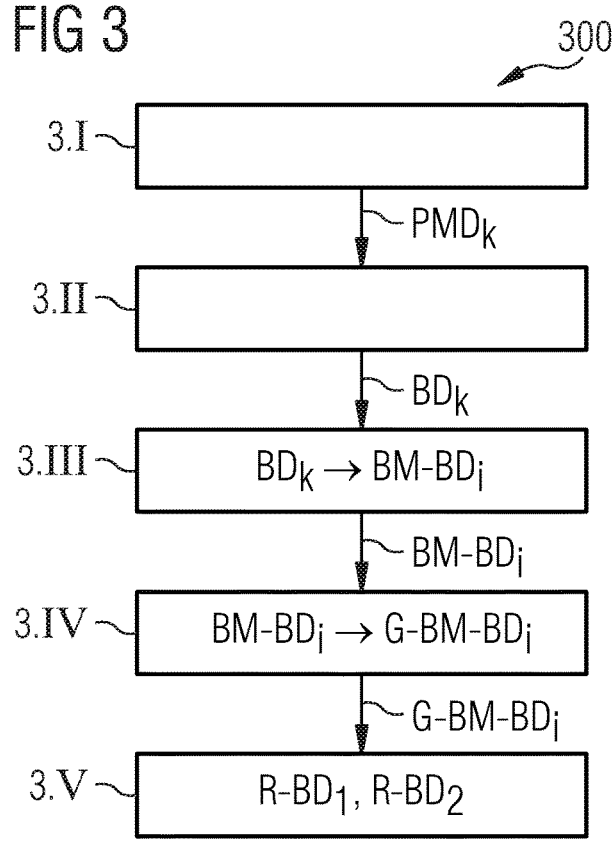
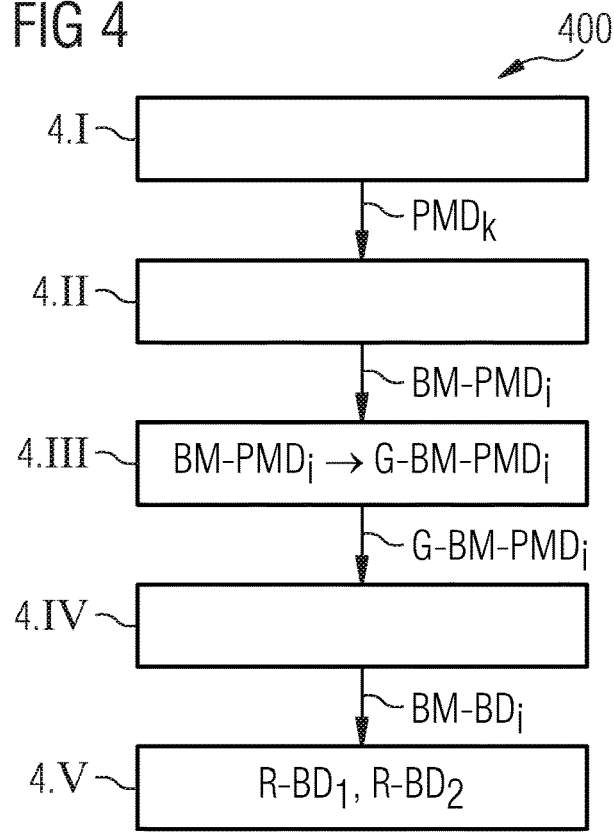

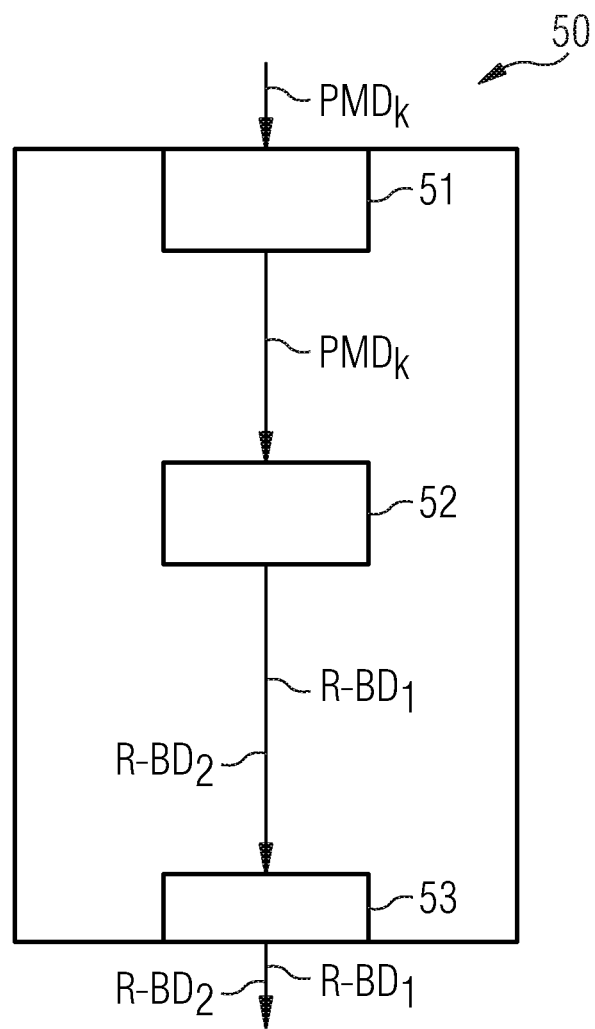

REDUCING THE NUMBER OF SPECTRAL CHANNELS IN MULTI-ENERGY CT IMAGING

PRIORITY STATEMENT

The present application hereby claims priority under 35 U.S.C. § 119 to German patent application number DE 102017200032.5 filed Jan. 3, 2017, the entire contents of which are hereby incorporated herein by reference.

FIELD

At least one embodiment of the invention generally relates to a method for the reconstruction of image data on the basis of a plurality of multi-energy projection measurement data sets for a field of examination of an object under examination. At least one embodiment of the invention moreover generally relates to an image data reconstruction facility. The invention furthermore relates to a computed tomography system.

BACKGROUND

With the aid of modern imaging methods two- or three-dimensional image data is often produced which can be utilized for visualizing an imaged object under examination and in addition also for other applications.

The imaging methods are often based on the capture of X-ray radiation, where so-called projection measurement data is produced. For example, projection measurement data can be acquired with the aid of a computed tomography system (CT system). In CT systems a combination which is arranged on a gantry and which comprises an X-ray source and an oppositely arranged X-ray detector usually rotates around a measurement chamber in which the object under examination (which is referred to in the following without limiting the generality as the patient) is situated. In this situation the center of rotation (also referred to as "isocenter") coincides with a so-called system axis z. During one or more rotations the patient is irradiated with X-ray radiation from the X-ray source, in which case projection measurement data or X-ray projection data which describes the X-ray attenuation of the patient in this direction of irradiation is captured with the aid of the oppositely arranged X-ray detector.

The projection measurement data produced, also referred to as projection data for short, is in particular dependent on the type of construction of the X-ray detector. X-ray detectors usually comprise a plurality of detection units which are mostly arranged in the form of a regular pixel array. The detection units in each case produce a detection signal for X-ray radiation impinging on the detection units which is analyzed at specific points in time in respect of intensity and spectral distribution of the X-ray radiation in order to provide information on the object under examination and to produce projection measurement data.

With certain types of CT imaging methods a plurality of imaging operations using X-ray radiation having different X-ray energy spectra are performed on one and the same field of examination of a patient. This process is also referred to as multi-energy CT imaging. Such multi-energy CT imaging can for example be performed with the aid of multiple successive CT imaging operations having a differing tube voltage. It is also possible to simultaneously implement imaging operations having differing energy spectra if an energy-sensitive detector is used and in the case of a single CT imaging operation X-ray attenuation data is recorded with differing effective spectra at the same time. This approach can for example be implemented with the aid of quantum-counting detectors or multi-layer detectors.

As a result of recording the same object using n differing energy spectra, where n is an integer, the amount of data is likewise increased in comparison with a single-energy CT imaging operation by the factor n. In consequence of the increased amount of data, in the case of multi-energy CT imaging operations problems can occur with regard to the transfer of data within a CT scanning unit. In addition, the long-term storage of the recorded data can be very complex.

Most known clinical evaluation methods are designed for dual-energy CT imaging operations, in other words CT imaging operations using only two differing X-ray energy spectra. A problem therefore consists in the fact that in the event of more than two energy spectra the existing methods can no longer be directly employed. For example, there are automated methods which use dual-energy CT image data sets as the basis for automatically differentiating kidney stone types or subtracting contrast agents from image data so that the body's own underlying tissue becomes visible. These applications cannot however be employed directly if more than two X-ray energy spectra have been used for the CT imaging operation.

SUMMARY

The inventors have recognized that a problem therefore resides in being able to apply existing methods for the evaluation of dual-energy CT image data without algorithmic changes to multi-energy CT image data. Generally speaking this is not possible without loss of information. If only two of the existing n data sets (where n>2) are processed, the advantages of the additional spectra are lost. This also applies in the case where simple mean values are formed between data sets and the mean values are processed further.

The inventors have recognized that a further problem with the processing of multi-energy CT data consists in the fact that during the recording thereof noise correlations occur between the differing data sets. The noise correlations can make spectral evaluation of the CT image data more difficult. It is therefore desirable to eliminate the noise correlations.

Conventionally, generally known methods for data compression are employed in order to reduce the amount of data. Conventionally, an attempt is also made in part to save spectral bands having reduced spatial or temporal resolution. In this situation however, a loss of radiofrequency information automatically occurs which must subsequently be restored.

The inventors have recognized that a problem therefore is to simplify the processing and evaluation of multi-energy CT data while maintaining the image quality.

At least one embodiment of the present invention is directed to a method for the reconstruction of image data on the basis of a plurality of multi-energy projection measurement data sets. At least one further embodiment of the present invention is directed to an image data reconstruction facility. Finally, at least one further embodiment of the present invention is directed to a computed tomography system.

With regard to the method according to at least one embodiment of the invention for the reconstruction of image data on the basis of a plurality of multi-energy projection measurement data sets for a field of examination of an object under examination, a plurality of projection measurement data sets are captured which have been produced with the aid of multi-energy CT imaging using differing X-ray energy spectra of the field of examination of the object under examination. On the basis of the plurality of projection measurement data sets, a reduced number of image data sets are subsequently produced by applying a basic material decomposition and an image mix.

The image data reconstruction facility according to at least one embodiment of the invention comprises a projection measurement data acquisition unit for capturing a plurality of projection measurement data sets which have been produced with the aid of multi-energy CT imaging using differing X-ray energy spectra of a field of examination of an object under examination. In addition, the image data reconstruction facility according to at least one embodiment of the invention comprises a reduction unit for producing a reduced number of image data sets on the basis of the plurality of projection measurement data sets by applying a basic material decomposition and an image mix.

The computed tomography system according to at least one embodiment of the invention has a scanning unit for scanning a field of examination of an object to be examined, a control device for driving the scanning unit and an image data reconstruction facility according to at least one embodiment of the invention. In this case the projection measurement data of a field of examination of an object under examination recorded by the computed tomography system is processed directly by the control device such that a reduced number of reconstructed image data sets having a differing X-ray energy spectrum are produced therefrom. Since the image data reconstruction facility is integrated directly in the computed tomography system, no additional devices are required outside of the CT system in order to perform a determination of a reduced number of image data sets.

A largely software-based implementation has the advantage that control devices of computed tomography systems or also other computer systems employed for analysis and evaluation which have already been used previously can also be upgraded in a simple manner by way of a software update in order to operate in an inventive manner. In this regard, at least one embodiment of the invention is also achieved by a corresponding computer program product having a computer program which can be loaded directly into a storage device of a computed tomography system according to at least one embodiment of the invention or another computer unit, having program sections in order to perform all the steps of the method according to at least one embodiment of the invention when the computer program is executed in the computed tomography system or another computer unit used for the evaluation of the projection measurement data and image data produced by the computed tomography system.

In addition to the computer program, such a computer program product can where applicable include additional elements such as for example documentation and/or additional components, also hardware components such as for example hardware keys (dongles etc.) for using the software.

A computer-readable medium, for example a memory stick, a hard disk or some other transportable or fixedly installed data medium on which the program sections of the computer program which can be read in and executed by a computer unit are stored can be used for transportation to the storage device of the computed tomography system or of the computer unit and/or for storage on the computed tomography system or on the computer unit. To this end, the computer unit can for example have one or more interoperating microprocessors or the like.

The claims and also the following description in each case contain particularly advantageous embodiments and developments of the invention. In this situation the claims in a claim category can in particular also be developed analogously to the dependent claims in a different claim category. In addition, the different features of various example embodiments and claims can also be combined in the context of the invention to produce new example embodiments.

BRIEF DESCRIPTION OF THE DRAWINGS

The invention will be described again in detail in the following with reference to the attached figures on the basis of example embodiments. In the drawings:

FIG. 1 shows a flowchart which illustrates a method for the reconstruction of image data on the basis of a plurality of multi-energy projection measurement data sets for a field of examination of an object under examination in accordance with a first example embodiment of the invention, FIG. 2 shows a flowchart which illustrates a method for the reconstruction of image data on the basis of a plurality of multi-energy projection measurement data sets for a field of examination of an object under examination in accordance with a second example embodiment of the invention, FIG. 3 shows a flowchart which illustrates a method for the reconstruction of image data on the basis of a plurality of multi-energy projection measurement data sets for a field of examination of an object under examination in accordance with a third example embodiment of the invention, FIG. 4 shows a flowchart which illustrates a method for the reconstruction of image data on the basis of a plurality of multi-energy projection measurement data sets for a field of examination of an object under examination in accordance with a fourth example embodiment of the invention, FIG. 5 shows a block diagram which illustrates an image data reconstruction facility in accordance with an example embodiment of the invention.

DETAILED DESCRIPTION OF THE EXAMPLE EMBODIMENTS

Figure 6:
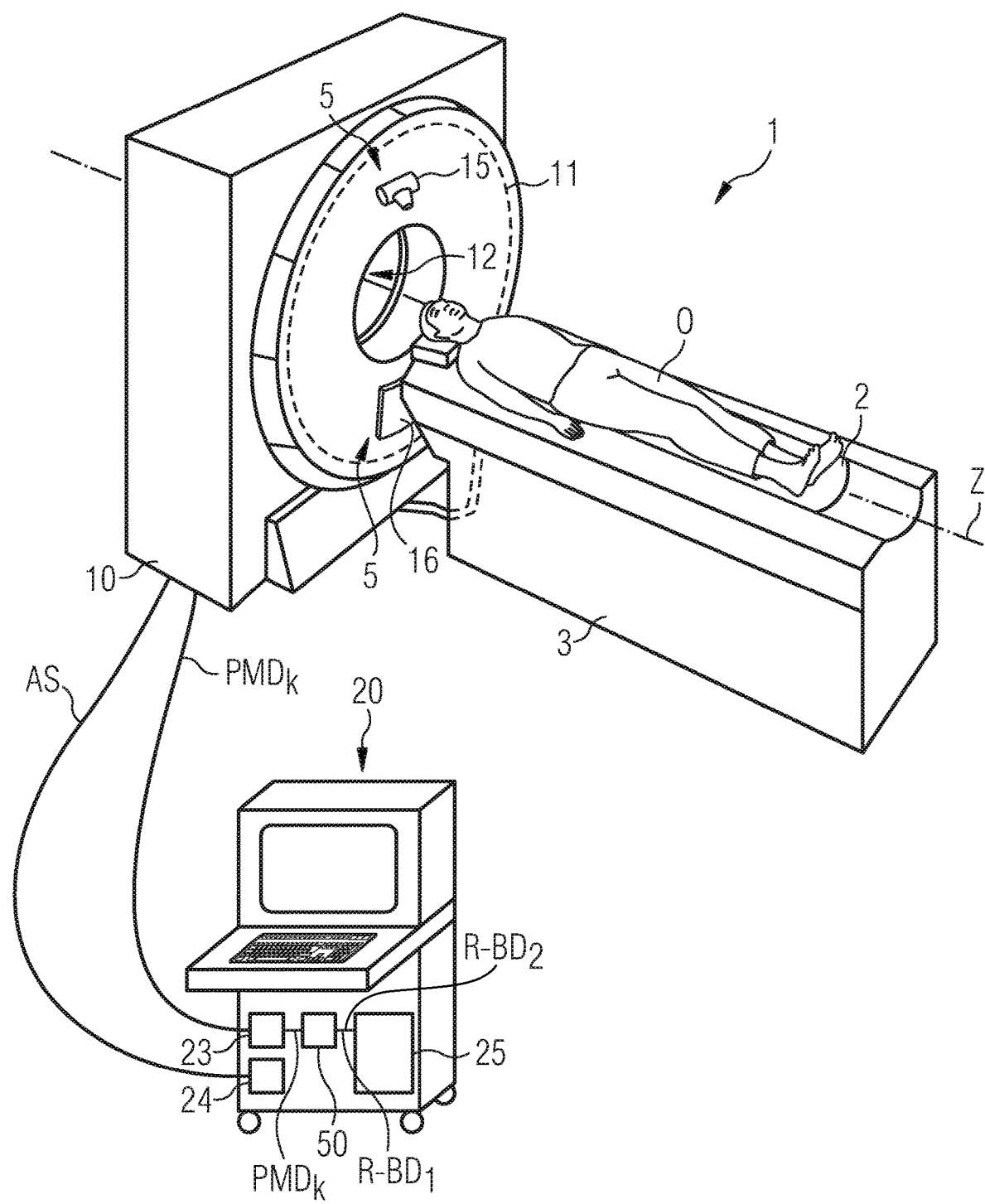
FIG. 6 shows a computed tomography system having an image data reconstruction facility in accordance with an example embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices.

The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

With regard to the method according to an embodiment of the invention for the reconstruction of image data on the basis of a plurality of multi-energy projection measurement data sets for a field of examination of an object under examination, a plurality of projection measurement data sets are captured which have been produced with the aid of multi-energy CT imaging using differing X-ray energy spectra of the field of examination of the object under examination. On the basis of the plurality of projection measurement data sets, a reduced number of image data sets are subsequently produced by applying a basic material decomposition and an image mix.

The reduced number corresponds to the number of basic materials which are produced during the basic material decomposition. The number of basic materials results from the number of physical effects which are relevant with regard to the attenuation of the X-ray radiation. As a rule, in the case of X-ray radiation having an energy of more than 35 keV and an atomic number of the existing atoms less than 55 the Compton effect and the photoelectric effect are relevant. In this case the decomposition of the captured data according to two basic materials is therefore sufficient. Methods for producing a basic material decomposition with two basic materials are known for example from Robert E. Alvarez and Albert Macovski, "Energy-selective reconstructions in X-ray computerized tomography", Phys. Med. Biol., 1976, vol. 21, no. 5, p. 733-744, the entire contents of which are hereby incorporated herein by reference.

If atoms having an atomic number greater than or equal to 55 are present in significant numbers in the field of examination, then a basic material decomposition takes place according to a total of three basic materials. Such a basic material decomposition is known from S. J. Riederer and C. A. Mistretta, "Selective iodine imaging using K-edge energies in computerized x-ray tomography", Medical Physics, vol. 4, no. 6, p. 474-481, November/December 1977, the entire contents of which are hereby incorporated herein by reference.

The basic material decompositions described in the literature are often based on the fact that the number of spectral channels measured is identical to the number of basic materials necessary in order to describe the X-ray attenuation. The general case having a greater number of basic materials than spectral channels can be found in Faby et al., "Performance of today's dual energy CT and future multi energy CT in virtual non-contrast imaging and in iodine quantification: A simulation study", Medical Physics, vol. 42, no. 7, p. 4349-4366, July 2015, the entire contents of which are hereby incorporated herein by reference. The case of statistical correlations of the input data is also dealt with therein.

It may also be expedient to break down this solution into two steps: In the first step statistical correlations are eliminated (decorrelator) and in the second step a mathematically more simple basic material decomposition is performed for uncorrelated data.

For decorrelation purposes a covariance matrix of the image noise is firstly ascertained. This can be ascertained for example on the basis of CT values measured on a homogeneous object or ideally on a calibration phantom optimized for the task.

Subsequently, by way of a linear mixing of the output images the covariance matrix can be converted into a diagonal matrix by ascertaining the eigenvectors and eigenvalues of the covariance matrix. In this situation however the CT value scale must be maintained, which means that a subsequent normalization is required.

More specifically, the linear mixing of the output images or the transformation matrix M describing the mix can be determined as follows:

From the eigenvalues of the covariance matrix a diagonal matrix Ep is ascertained, on the main diagonals of which in the i-th row and the i-th column in each case stands the −0.5-th power of the i-th eigenvalue. From the normalized eigenvectors of the covariance matrix is formed a matrix L having the eigenvectors as column vectors. Finally, an arbitrary n-dimensional rotation matrix R is formed.

The transformation matrix M then results as follows:

$$M = R \cdot Ep \cdot L^T. \quad (1)$$

The transformation matrix must still be normalized by requiring that the CT value of air, in other words −1000 HU, must be maintained under the transformation. To this end an n-dimensional vector t is needed in which each element exhibits the value −1000 HU.

If the vector t is multiplied by the transformation matrix M, then a vector tp possibly deviating from t is obtained. The normalizations normy$_i$ then result from the elements tp$_i$ of the vector tp:

$$\text{normy}_i = -1000 \text{ HU}/tp_i. \quad (2)$$

The normalized transformation matrix M$_{norm}$ then results therefrom by multiplying each row i of the matrix M by the normalization value normy$_i$.

The rotation matrix R is in principle freely selectable. It can for example however be chosen such that the image noise in the decorrelated image data sets is in each case of approximately equal magnitude.

Mathematically it is also possible to determine the transformation matrix M in a different manner; in particular for this purpose it is not absolutely necessary to determine eigenvalues or eigenvectors of the covariance matrix. For example, the image values measured in a water phantom in a region can be entered in one vector each per spectrum. Given the correct calibration for water the mean values of the vectors are 0 HU.

If the image noise is correlated, the scalar products between the vectors will however be not equal to zero.

A transformation matrix M can now be determined by searching with the aid of the Gram-Schmidt orthogonalization process for an orthogonal basis in the space of the measured vectors. The normalized transformation matrix is subsequently ascertained again as described above.

The decorrelation of the spectral channels has the principal advantage that the uncorrelated result data is better suited for many analysis algorithms than the strongly correlated input data. It is therefore useful even without a subsequent reduction in the spectral channels.

If a basic material decomposition is to be performed after the decorrelation, then the nominal CT values of the basic materials must be transformed in the same manner as the CT image data.

The already ascertained normalized transformation matrix $M_{norm}$ can be used for the transformation of the basic materials.

After the basic material decomposition has been performed, a reduced number of at least 2 sets of basic material images are present. The basic material images have various disadvantages for the further processing: On the one hand they differ significantly from regular CT images; thus for example hardly any soft tissue structures show up on the iodine basic material images and the scaling can differ significantly from regular CT images. On the other hand they are statistically strongly correlated.

It is therefore expedient in the context of an image mix from the basic material images to again produce by way of a linear combination an equal number of CT images which follow the usual scaling; in other words water has the value 0 HU in all images and air has the value −1000 HU in all images. Statistical correlations between the images can if necessary be eliminated by possible renewed use of the decorrelator. The result images then correspond to CT images which have been produced using other, possibly also monochromatic output spectra.

The method according to at least one embodiment of the invention offers an efficient approach for an optimum reduction in the number of energy spectra during multi-energy CT imaging, in particular to two or three energy spectra, with regard to the evaluation of CT imaging operations having more than two or three energy spectra. On account of the reduction in the number of energy spectra or the corresponding image data sets, noise effects are reduced in the reconstructed image data sets. Furthermore, on account of the sharp reduction in the number of image data sets there results a dramatic saving in storage space for image data to be saved. In addition, on account of the data reduction the image processing is significantly simplified and accelerated.

For the case that material having a very high atomic number are present in the region to be examined, it may also be appropriate to perform a decomposition into more than three basic materials.

The image data reconstruction facility according to at least one embodiment of the invention comprises a projection measurement data acquisition unit for capturing a plurality of projection measurement data sets which have been produced with the aid of multi-energy CT imaging using differing X-ray energy spectra of a field of examination of an object under examination. In addition, the image data reconstruction facility according to at least one embodiment of the invention comprises a reduction unit for producing a reduced number of image data sets on the basis of the plurality of projection measurement data sets by applying a basic material decomposition and an image mix.

The computed tomography system according to at least one embodiment of the invention has a scanning unit for scanning a field of examination of an object to be examined, a control device for driving the scanning unit and an image data reconstruction facility according to at least one embodiment of the invention. In this case the projection measurement data of a field of examination of an object under examination recorded by the computed tomography system is processed directly by the control device such that a reduced number of reconstructed image data sets having a differing X-ray energy spectrum are produced therefrom. Since the image data reconstruction facility is integrated directly in the computed tomography system, no additional devices are required outside of the CT system in order to perform a determination of a reduced number of image data sets.

The main components of the image data reconstruction facility according to at least one embodiment of the invention can be designed for the most part in the form of software components. This concerns in particular parts of the projection measurement data acquisition unit and the reduction unit. In principle, the components can however also be implemented partly in the form of software-supported hardware components, for example FPGAs or the like, in particular if the calculations in question are particularly fast. Likewise, the required interfaces can, for example if it is only a question of a transfer of data from other software components, be designed as software interfaces. They can however also be designed as interfaces built on a hardware basis which are driven by suitable software.

A largely software-based implementation has the advantage that control devices of computed tomography systems or also other computer systems employed for analysis and evaluation which have already been used previously can also be upgraded in a simple manner by way of a software update in order to operate in an inventive manner. In this regard, at least one embodiment of the invention is also achieved by a corresponding computer program product having a computer program which can be loaded directly into a storage device of a computed tomography system according to at least one embodiment of the invention or another computer unit, having program sections in order to perform all the steps of the method according to at least one embodiment of the invention when the computer program is executed in the computed tomography system or another computer unit used for the evaluation of the projection measurement data and image data produced by the computed tomography system.

In addition to the computer program, such a computer program product can where applicable include additional elements such as for example documentation and/or additional components, also hardware components such as for example hardware keys (dongles etc.) for using the software.

A computer-readable medium, for example a memory stick, a hard disk or some other transportable or fixedly installed data medium on which the program sections of the computer program which can be read in and executed by a computer unit are stored can be used for transportation to the storage device of the computed tomography system or of the computer unit and/or for storage on the computed tomography system or on the computer unit. To this end, the computer unit can for example have one or more interoperating microprocessors or the like.

In an embodiment of the method according to the invention for the reconstruction of image data on the basis of a plurality of multi-energy projection measurement data sets for a field of examination of an object under examination, in the step for producing a reduced number of image data sets a corresponding plurality of image data sets are firstly reconstructed on the basis of the plurality of projection measurement data sets. Reconstruction should be understood in the entire application as being a transformation of projection data from the raw data space or projection data space into the image data space. The transformation applied in this situation corresponds to a radon transformation. A decorrelation process is furthermore applied to the plurality of image data sets, wherein decorrelated image data is produced. The decorrelation of the image data can be performed in accordance with the approach already described. Finally, a basic material decomposition takes place on the basis of the decorrelated image data. In this situation the number of image data sets is reduced to the number of basic materials. The number of basic materials typically has the value 2. This applies in the event that the atomic numbers of the atoms in the field of examination are less than 55 and the energy of the X-rays used for imaging is greater than 35 keV. If atoms having atomic numbers greater than or equal to 55 are present in the field of examination, then the number of basic materials has the value 3 or greater. With regard to the image mix, in the context of this embodiment the reduced number of basic material image data sets is summed in linearly weighted fashion in such a manner that correlated or decorrelated image data is produced with attenuation values which correspond to differing polychromatic or monochromatic X-ray energy spectra. In this manner image displays are produced which correspond to CT images which have been recorded using differing polychromatic or monochromatic X-ray energy spectra.

In a preferred embodiment of the method according to an embodiment of the invention for the reconstruction of image data on the basis of a plurality of multi-energy projection measurement data sets for a field of examination of an object under examination, when producing a reduced number of image data sets a decorrelated basic material decomposition is applied to the plurality of projection measurement data sets by multiplying the projection measurement data sets by a mixing matrix. In this situation the mixing matrix is constructed in such a manner that when it is used a reduced number of decorrelated projection data sets is produced. Finally, a reduced number of decorrelated image data sets is reconstructed on the basis of the decorrelated projection data sets. Since with this variant the reconstruction step is applied to decorrelated projection data sets which are already reduced in number, the reconstruction is significantly simplified and accelerated in this case. The mixing matrix can for example be produced firstly in the image space on the basis of decorrelated image data by way of the described decorrelation process and additionally the described step for producing a basic material decomposition. On account of the linearity of the image reconstruction the matrix can also be used in the raw data space or projection data space, in other words it can also be applied directly to the plurality of multi-energy projection measurement data sets. The mixing matrix moreover also performs a mixing function, where this variant is carried out in the raw data space or projection data space.

By preference, with regard to the method according to an embodiment of the invention for the reconstruction of image data on the basis of a plurality of multi-energy projection measurement data sets for a field of examination of an object under examination, in the step for producing a reduced number of image data sets the decorrelation process is applied after the basic material decomposition in order to obtain a best possible mean value of the basic material images for at least one basic material by determining a weighted mean value after decorrelation (spectral weighting). In this situation a weighting of basic material image data sets or basic material projection data sets which describe the same basic material but have been produced from differing combinations of single-energy imaging operations, in other words using differing X-ray energy spectra, is undertaken in such a manner that noise effects or artifact effects are reduced. With this variant, n basic material image data sets or basic material projection measurement data sets are originally available. These are grouped in pairs for m=2 and a basic material decomposition is applied to the i pairs resulting from the grouping, where $i<=n!/(2!\times(n-2)!)$.

In this situation, as a general rule not all pairs will enable a good result quality, which means that not all possible combinations are possible or necessary. Basic material decompositions according to the same two basic materials are performed in each case for the i pairs. A total of i images are then obtained for each basic material which in principle show the same, but have differing noise and moreover are correlated in the noise. Only after the spectral weighting has been performed are the required final basic material images then obtained from the respective i basic material images per basic material for example by forming a weighted mean value after the decorrelation, where the weight of each material image is 1/variance of the image noise. For the weighting function advantage is taken of the fact that as a general rule for physical reasons a raw data based basic material decomposition can be unambiguously resolved into a reduced number of materials for each combination of a correspondingly reduced number of X-ray energy spectra. Only noise effects and measurement errors differ according to the choice of the spectra used. This statement makes it possible to solve the generally complicated problem of finding an optimal mapping of a number of image data sets to a reduced number of basic materials as a result of the fact that these are ascertained as a weighted mean value by way of a number of i basic material decompositions.

In this particularly advantageous variant of the method according to an embodiment of the invention for the reconstruction of image data on the basis of a plurality of multi-energy projection measurement data sets for a field of examination of an object under examination, in the step for producing a reduced number of image data sets a corresponding plurality of image data sets are therefore reconstructed on the basis of the plurality of projection measurement data sets. Subsequently the basic material decomposition takes place on the basis of the image data sets, wherein at least two differing combinations of image data sets are used for each basic material. In other words, a plurality of basic material decompositions are produced, where each of the basic material decompositions is based only on a part of the image data sets.

In a particularly advantageous embodiment of the method according to an embodiment of the invention for the reconstruction of image data on the basis of a plurality of multi-energy projection measurement data sets for a field of examination of an object under examination, in the step for producing a reduced number of image data sets a reduced number is selected from the plurality of projection measurement data sets and a corresponding number of basic material projection data sets is produced with the aid of the basic material decomposition from the reduced number of projection measurement data sets. This process takes place with differing combinations of projection measurement data sets, with the result that a plurality of basic material decompositions are produced, each of which is based only on a part of the projection measurement data sets.

In another variant of the method according to an embodiment of the invention for the reconstruction of image data on the basis of a plurality of multi-energy projection measurement data sets for a field of examination of an object under examination, in the step for producing a reduced number of image data sets a corresponding number of basic material image data sets is reconstructed on the basis of the reduced number of basic material projection data sets. This process again takes place on the basis of a plurality of basic material decompositions, each of which comprises a reduced number of basic material projection data sets. In this manner a plurality of groups of basic material image data sets are produced. These differing groups of basic material image data sets are subsequently subjected to a decorrelation and added in weighted fashion with the aid of a spectral weighting in accordance with their information content, with the result that a single group of a reduced number of basic material image data sets is created, which exhibit an optimum noise weighting.

In a special embodiment of the method according to an embodiment of the invention for the reconstruction of image data on the basis of a plurality of multi-energy projection measurement data sets for a field of examination of an object under examination, in the step for producing a reduced number of image data sets a decorrelation of the basic material projection data and a spectral weighting are undertaken on the basis of the reduced number of basic material projection data sets, by which an optimum noise weighting is achieved, and a corresponding reduced number of weighted and decorrelated basic material image data sets is reconstructed on the basis of the weighted basic material projection data sets obtained as a result of the spectral weighting.

By preference, in the context of the method according to an embodiment of the invention in the step for producing a reduced number of image data sets the reduced number of basic material image data sets is summed on the basis of the plurality of projection measurement data sets in linearly weighted fashion in such a manner that decorrelated image data is produced with attenuation values which correspond to differing, for example monochromatic X-ray energy spectra. Methods for calculating single-energy images are known for example from Yu L. et al, "Virtual monochromatic imaging in dual-source dual-energy CT: radiation dose and image quality", Med. Phys. 2011 December; 38(12):6371-9, the entire contents of which are hereby incorporated herein by reference. However, the described variant goes beyond the known approach to the extent that a reduced number of images is defined, the image noise whereof is mutually orthogonal. The images produced are therefore completely decorrelated as far as regards the noise behavior. The image noise thus behaves in exactly the same way as in the case of imaging methods which on their own produce uncorrelated multi-energy CT images. This is the case for example if a plurality of CT scans are carried out successively using a differing tube voltage and a conventional X-ray detector. The statistical independence is particularly relevant in the case of methods employed in multi-energy CT for noise reduction. To this end reference should be made to DE 10 2011 083 727 A1, the entire contents of which are hereby incorporated herein by reference.

In a particularly widely used variant of the method according to an embodiment of the invention for the reconstruction of image data on the basis of a plurality of multi-energy projection measurement data sets for a field of examination of an object under examination, the reduced number of image data sets has the value 2. As already mentioned, this variant is utilized if in the case of a CT imaging operation in the field of examination only atoms having an atomic number Z<55 occur in relevant numbers and the energy of the X-rays does not fall below a value of 35 keV.

In an alternative variant the reduced number of image data sets has the value 3. This variant is utilized if in the case of a CT imaging operation in the field of examination precisely one type of atom having an atomic number Z>55 occurs in relevant numbers.

FIG. 1 shows a flowchart 100 which illustrates a method for the reconstruction of image data on the basis of a plurality of multi-energy projection measurement data sets for a field of examination of an object under examination in accordance with a first example embodiment of the invention. In the method, an acquisition of multi-energy projection measurement data firstly takes place in step 1.I. The multi-energy projection measurement data comprises n projection measurement data sets $PMD_k$, where k=1 to n, with each of which is associated a differing energy spectrum which was used for recording the respective projection measurement data set $PMD_k$. Subsequently in step 1.II image data is reconstructed on the basis of the multi-energy projection measurement data. The image data in turn comprises n image data sets $BD_k$, where k=1 to n and a corresponding image data set $BD_k$ is reconstructed from each projection measurement data set $PMD_k$.

Following the image data reconstruction, a decorrelation of the image data takes place in step 1.III. In this case the image data sets $BD_k$ with n different spectra are used as input and n new image data sets $D\text{-}BD_k$ without statistical correlations in respect of the image noise behavior are produced therefrom. In this situation the CT values of the materials change, which means that the result images $D\text{-}BD_k$ correspond to other photon spectra than the input images $BD_k$. The decorrelation is performed for example with the aid of linear algebra methods and is not unambiguous, in other words given the same image data $BD_k$ as input data, different sets of uncorrelated result images $D\text{-}BD_k$ may be produced.

Subsequently in step 1.IV the actual decomposition of the n decorrelated image data sets $D\text{-}BD_k$ into m basic material images $D\text{-}BM\text{-}BD_i$ takes place, wherein the integer m is less than the integer n and i=1 to m. The number m corresponds to the number of differing physical effects which occur during the X-ray examination. For X-ray spectra having energies above 35 keV and an atomic number less than 55 these are the photoelectric effect and the Compton effect, which means that m has the value 2 in this case. In the case of the image-based m material decomposition an optimization process is used for this purpose, which for example encompasses a "least-square fit". This process involves the method of least squares. Since the basic material decomposition is a linear operation, the results of a "least-square fit" can for example be determined unambiguously and analytically. The "least-square fit" furthermore has the property that differing decorrelations of the same image data result in the same basic material images. The combination of decorrelation and basic material decomposition thereby delivers unambiguous results at least when a "least-square fit" is used.

Finally, in step 1.V a single-energy image mix takes place. In a single-energy image mix the basic material images D-BM-BD$_i$ ascertained are again summed in weighted fashion in such a manner that regular CT values are created which would have also been obtained with a regular CT imaging operation performed on the same object with a single photon spectrum. With single-energy image mixing, for the case m=2 precisely two CT images R-BD$_1$, R-BD$_2$ (in the general case precisely m CT images) are produced which correspond to differing monochromatic photon spectra. Ideally these images are statistically uncorrelated. In order to achieve this decorrelation, with single-energy image mixing the patient diameter or the patient attenuation must also be taken into consideration and the equivalent energies of the output images must be adjusted in accordance with defined rules. In this manner, result images R-BD$_1$, R-BD$_2$ are obtained which behave like "normal" CT images.

With the method, illustrated in FIG. 2, in accordance with a second example embodiment of the invention, as with the method shown in FIG. 1 multi-energy projection measurement data is firstly acquired in step 2.I. The multi-energy projection measurement data again comprises n projection measurement data sets PMD$_k$, where k=1 to n, with each of which is associated a differing X-ray energy spectrum which was used for recording the respective projection measurement data set PMD$_k$. Subsequently in step 2.II, differently from the first example embodiment illustrated by FIG. 1, a linear raw data mix takes place in the second example embodiment shown in FIG. 2. In other words, the n projection measurement data sets PMD$_k$ having n differing spectra are converted in the raw data space into m decorrelated projection data sets D-PMD$_l$, where l=1 to m and m<n. To this end a simple two-dimensional matrix is used in order to convert the attenuation values or CT values into one another. The matrix is constructed such that it results approximately directly in decorrelated data sets. Such a matrix, also referred to as a mixing matrix, can in this situation be produced on the basis of the decorrelation process and basic material decomposition process described by the steps 1.III and 1.IV. In addition the mixing matrix also performs a mixing function corresponding to the image mixing described in step 1.V in conjunction with FIG. 1, where the mixing function takes place in the raw data space or projection data space in step 2.II.

Finally, a reconstruction of the m decorrelated projection data sets D-PMD$_i$ to form m decorrelated image data sets D-BD$_i$ takes place in step 2.III.

With the method shown in FIG. 3 for the reconstruction of image data on the basis of a plurality of multi-energy projection measurement data sets for a field of examination of an object under examination in accordance with a third example embodiment, by analogy with the first example embodiment an acquisition of multi-energy projection measurement data firstly takes place in step 3.I. The multi-energy projection measurement data comprises n projection measurement data sets PMD$_k$, wherein k=1 to n, with each of which is associated a differing X-ray energy spectrum which was used for recording the respective projection measurement data set PMD$_k$. Subsequently in step 3.II, by analogy with the first example embodiment shown in FIG. 1, image data is reconstructed on the basis of the multi-energy projection measurement data sets PMD$_k$, where again n image data sets BD$_k$ are produced, where k=1 to n and each of the n image data sets BD$_k$ is reconstructed from a projection measurement data set PMD$_k$. Subsequently in step 3.III, differently from the first example embodiment shown in FIG. 1, initially no decorrelation of the reconstructed image data sets BD$_k$ is yet performed but a decomposition of the n image data sets BD$_k$ into m basic material image data sets BM-BD$_i$ takes place directly. In this situation a plurality of differing combinations of m image data sets are however utilized, which means that a plurality of groups of m basic material image data sets BM-BD$_i$ are also created.

In step 3.IV a spectral weighting is then performed in each case of the groups of m basic material image data sets BM-BD$_i$, where weighted m basic material image data sets G-BM-BD$_i$ are produced. With the spectral weighting, basic material images which in each case describe the same basic material but have been obtained from differing combinations of source spectra are weighted in such a manner that the noise behavior and the artifact level are minimized. The noise of the basic material images may be correlated. In this case the correlation must be taken into consideration during the determination of the optimum weighting function. The spectral weighting function depends in any form on the patient diameter or the patient attenuation. For example, in the case of larger diameters contributions from combinations of low-energy spectra are weighted more weakly than contributions from combinations of high-energy spectra. As the result of the spectral weighting only one image data set is obtained per basic material.

Finally, by analogy with step 1.V a single-energy image mix is performed again in step 3.V. During the single-energy image mix the weighted basic material images G-BM-BD$_i$ ascertained are again summed in weighted fashion in such a manner that regular CT values are created which would have also been obtained with a regular CT imaging operation performed on the same object with a single photon spectrum. With single-energy image mixing, for the case m=2 precisely two CT images R-BD$_1$, R-BD$_2$ (in the general case precisely m CT images) are accordingly produced which correspond to differing monochromatic photon spectra. Ideally these images are statistically uncorrelated. In order to achieve this decorrelation, with single-energy image mixing the patient diameter or the patient attenuation must also be taken into consideration and the equivalent energies of the output images must be adjusted in accordance with defined rules.

With the method shown in FIG. 4 for the reconstruction of image data on the basis of a plurality of multi-energy projection measurement data sets for a field of examination of an object under examination in accordance with a fourth example embodiment, by analogy with the first example embodiment an acquisition of multi-energy projection measurement data comprising n projection measurement data sets PMD$_k$ firstly takes place in step 4.I. Subsequently in step 4.II an m material decomposition is performed on the basis of the raw data PMD$_k$. In this case, in similar fashion to step 3.III but this time in the raw data space instead of in the image data space, at least two differing combinations of m projection measurement data sets PMD$_k$ of the n projection measurement data sets PMD$_k$ are in each case decomposed into a group of m basic material projection measurement data sets BM-PMD$_i$.

Subsequently in step 4.III a spectral weighting of the groups of m basic material projection measurement data sets BM-PMD$_i$ takes place in similar fashion to step 3.IV, but this time in the raw data space. With the spectral weighting, in each case at least two basic material projection measurement data sets BM-PMD$_i$, which in each case describe the same basic material but have been obtained from differing combinations of source spectra or differing groups of basic material projection measurement data sets BM-PMD$_i$, are weighted in such a manner that the noise behavior and the artifact level are minimized. The noise of the basic material projection measurement data BM-PMD$_i$ may be correlated. In this case the correlation must be taken into consideration during the determination of the optimum weighting function. The spectral weighting function depends in any form on the patient diameter or the patient attenuation. For example, in the case of larger diameters contributions from combinations of low-energy spectra are weighted more weakly than contributions from combinations of high-energy spectra. As the result of the spectral weighting only one basic material data set G-BM-PMD$_i$ is obtained per basic material.

In step 4.IV image data BM-BD$_i$ is reconstructed, where the image data BM-BD$_i$ again comprises m image data sets, where i=1 to m, with each of which is associated a projection measurement data set G-BM-PMD$_i$ originating from a spectral weighting.

Finally, in step 4.V a single-energy image mix is performed. In single-energy image mixing the basic material images BM-BD$_i$ ascertained are again summed in weighted fashion in such a manner that regular CT values are created which would have also been obtained with a regular CT imaging operation performed on the same object with a single photon spectrum. With single-energy image mixing (for the case m=2), precisely two CT images R-BD$_1$, R-BD$_2$ are produced which correspond to differing monochromatic photon spectra. Ideally these images are statistically uncorrelated. In order to achieve this decorrelation, with single-energy image mixing the patient diameter or the patient attenuation must also be taken into consideration and the equivalent energies of the output images must be adjusted in accordance with defined rules.

In a variation of the fourth example embodiment the steps 4.III and 4.IV are interchanged. In other words, the reconstruction takes place before the spectral weighting and instead of the weighting of basic material projection measurement data sets BM-PMD$_i$ in step 4.III the reconstructed basic material image data sets BM-BD$_i$ are then weighted spectrally in step 4.IV.

FIG. 5 shows a block diagram which schematically illustrates an image data reconstruction facility 50. The image data reconstruction facility 50 comprises a projection measurement data acquisition unit 51 for capturing a plurality n of projection measurement data sets PMD$_k$ which have been produced with the aid of multi-energy CT imaging using differing X-ray energy spectra of a field of examination of an object under examination O. The image data reconstruction facility 50 furthermore comprises a reduction unit 52 for producing a reduced number m of image data sets R-BD$_i$ (i=1 to m, m≥2) on the basis of the plurality n of projection measurement data sets PM by applying a basic material decomposition. The reduction unit is configured in order to perform one or more of the methods described in conjunction with FIG. 1 to FIG. 4. Finally, the image data reconstruction facility 50 also comprises an output interface 53 by which the ascertained reduced m image data sets R-BD$_1$, R-BD$_2$ are output.

FIG. 6 schematically illustrates a computed tomography system (CT system) 1 having an image data reconstruction facility 50 in accordance with an example embodiment of the invention. The CT system 1 is used for recording projection measurement data for a field of examination of a patient.

The CT system 1 consists essentially of a scanning unit 10, in which a projection data acquisition unit 5 arranged on a gantry 11 and having a detector 16 and an X-ray source 15 located opposite the detector 16 rotates around a measurement chamber 12. In front of the scanning unit 10 is situated a patient support device 3 or a patient examination table 3, the upper part 2 whereof can be slid toward the scanning unit 10 with a patient O situated thereon in order to move the patient O through the measurement chamber 12 relative to the detector system 16. The scanning unit 10 and the patient examination table 3 are driven by a control device 20, from which are received acquisition control signals AS by way of a normal control interface 24 in order to drive the entire system in the conventional manner in accordance with predefined measurement protocols. Due to the movement of the patient O along the z direction, which corresponds to the system axis z longitudinally through the measurement chamber 12, and the simultaneous rotation of the X-ray source 15 a helical path results for the X-ray source 15 relative to the patient O during the measurement. In this situation the detector 16 is always running in parallel opposite the X-ray source 15 in order to capture projection measurement data which is then used for the reconstruction of volume and/or slice image data. It is likewise also possible to perform a sequential measurement process in which a fixed position is approached in the z direction and then during one rotation, a partial rotation or a plurality of rotations at the z position in question the necessary multi-energy projection measurement data PMD$_k$ is captured in order to reconstruct a sectional image at the z position or in order to reconstruct volume image data from the projection data for a plurality of z positions. The method according to the invention can in principle also be employed on other CT systems, for example by using a detector forming a complete ring.

In the example embodiment shown in FIG. 6 the detector 16 is a quantum-counting detector, via which captured X-ray quanta can be captured resolved according to the X-ray energy. With the aid of the quantum-counting detector the captured X-ray quanta can be associated with differing X-ray energy spectra, which means that n multi-energy CT-projection measurement data sets PMD$_k$ are produced.

The projection measurement data sets PMD$_k$ acquired by the detector 16 for a field of examination of the patient O are passed by way of a raw data interface 23 to the control device 20. The projection measurement data sets PMD$_k$ are then reconstructed by a reconstruction facility 50 in accordance with an example embodiment of the invention in the manner described in FIG. 1 to FIG. 5 to form image data R-BD$_1$, R-BD$_2$.

Finally, it should be noted once again that the methods and devices described in the foregoing are only preferred example embodiments of the invention and that the invention can be varied by the person skilled in the art without departing from the scope of the invention, insofar as it is predetermined by the claims. It should also be noted for the sake of completeness that the use of the indefinite article "a" or "an" does not mean that the features in question cannot be present in a multiple manner. Likewise the term "unit" does not mean that these cannot consist of a number of components, which can in some instances also be spatially distributed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for reconstruction of image data based upon a plurality of multi-energy projection measurement data sets for a field of examination of an object under examination, the method comprising:
    capturing a plurality of projection measurement data sets, each of the plurality of projection measurement data sets being produced, via multi-energy CT imaging, using differing X-ray energy spectra of the field of examination of the object under examination, to produce a plurality of captured projection measurement data sets; and
producing a reduced number of image data sets based upon the plurality of captured projection measurement data sets, the reduced number of image data sets being fewer in number than the plurality of captured projection measurement data sets, by applying a basic material decomposition and an image mix, wherein the producing of the reduced number of image data sets comprises:
    applying a decorrelated basic material decomposition to the plurality of projection measurement data sets by multiplying the projection measurement data sets by a mixing matrix constructed to produce a reduced number of decorrelated projection data sets; and
    reconstructing a reduced number of decorrelated image data sets based upon the decorrelated projection data sets.

2. The method of claim 1, wherein the producing of the reduced number of image data sets comprises:
    reconstructing a corresponding plurality of image data sets based upon of the plurality of projection measurement data sets; and
    applying a decorrelation process to the plurality of image data sets, to produce decorrelated image data, the applying of the basic material decomposition taking place based upon the decorrelated image data, to produce a reduced number of basic material image data sets, and
    wherein the applying of the image mix to the reduced number of basic material image data sets includes summing, in a linearly weighted fashion, such that image data is produced with attenuation values which correspond to differing polychromatic or monochromatic X-ray energy spectra.

3. The method of claim 1, wherein the producing of the reduced number of image data sets includes a decorrelation process, taking place after the applying of the basic material decomposition, wherein a weighting of basic material image data sets or basic material projection data sets, associated with a same basic material but having been produced from differing combinations of single-energy imaging operations taking place to reduce noise effects or artifact effects.

4. The method of claim 3, wherein the producing of the reduced number of image data sets comprises:
    reconstructing a corresponding plurality of image data sets based upon the plurality of projection measurement data sets, wherein the basic material decomposition takes place based upon the image data sets and at least two differing combinations of single-energy imaging operations are used for each basic material.

5. The method of claim 3, wherein the producing of the reduced number of image data sets comprises
    selecting the reduced number from the plurality of projection measurement data sets and
    producing a corresponding reduced number of basic material projection data sets using basic material decomposition from a reduced number of the projection measurement data sets.

6. The method of claim 5, wherein the producing of the reduced number of image data sets comprises:
    reconstructing, based upon the reduced number of basic material projection data sets, a corresponding reduced number of basic material image data sets, the decorrelation process taking place based upon the reduced number of basic material image data sets produced, to subsequently undertake an optimum noise weighting.

7. The method of claim 5, wherein the producing of the reduced number of image data sets comprises:
    applying, based upon the reduced number of basic material projection data sets, the decorrelation process to subsequently undertake an optimum noise weighting to produce decorrelated and weighted basic material projection data sets, and
    reconstructing a corresponding number of basic material image data sets based upon the decorrelated and weighted basic material projection data sets.

8. The method of claim 1, wherein the producing of the reduced number of image data sets comprises:
    summing, based upon the plurality of projection measurement data sets, the reduced number of image data sets in a linearly weighted fashion such that image data is produced with attenuation values which correspond to differing polychromatic or monochromatic X-ray energy spectra.

9. The method of claim 1, wherein the reduced number of image data sets has a value of 2.

10. The method of claim 1, wherein the reduced number of image data sets has a value of 3.

11. An image data reconstruction device, comprising:
    memory storing computer-readable instructions; and one or more processors configured to execute the computer-readable instructions such that the one or more processors are configured to perform operations including, capturing a plurality of projection measurement data sets, the plurality of projection measurement data sets produced via multi-energy CT imaging using differing X-ray energy spectra of a field of examination of an object under examination, to produce a plurality of captured projection measurement data sets; and producing a reduced number of image data sets based upon the plurality of captured projection measurement data sets by applying a basic material decomposition and an image mix, the producing the reduced number of image data sets includes:

applying a decorrelated basic material decomposition to the plurality of projection measurement data sets by multiplying the projection measurement data sets by a mixing matrix constructed to produce a reduced number of decorrelated projection data sets; and reconstructing a reduced number of decorrelated image data sets based upon the decorrelated projection data sets.

12. A computed tomography system, comprising:
a scanner configured to scan a field of examination of an object to be examined;
a controller configured to drive the scanning unit; and
the image data reconstruction device of claim 11.

13. A non-transitory computer program product including a computer program, directly loadable into a storage device of a computed tomography system, including program sections to perform the method of claim 1 when the computer program is executed in the computed tomography system.

14. A non-transitory computer-readable medium, storing program sections, readable in and executable by a computer unit, to execute the method of claim 1 when the program sections are executed by the computer unit.

15. The method of claim 3, wherein the producing of the reduced number of image data sets comprises:
summing, based upon the plurality of projection measurement data sets, the reduced number of image data sets in a linearly weighted fashion such that image data is produced with attenuation values which correspond to differing polychromatic or monochromatic X-ray energy spectra.

16. The method of claim 4, wherein the producing of the reduced number of image data sets comprises:
summing, based upon the plurality of projection measurement data sets, the reduced number of image data sets in a linearly weighted fashion such that image data is produced with attenuation values which correspond to differing polychromatic or monochromatic X-ray energy spectra.

17. The method of claim 5, wherein the producing of the reduced number of image data sets comprises:
summing, based upon the plurality of projection measurement data sets, the reduced number of image data sets in a linearly weighted fashion such that image data is produced with attenuation values which correspond to differing polychromatic or monochromatic X-ray energy spectra.

18. The method of claim 6, wherein the producing of the reduced number of image data sets comprises:
summing, based upon the plurality of projection measurement data sets, the reduced number of image data sets in a linearly weighted fashion such that image data is produced with attenuation values which correspond to differing polychromatic or monochromatic X-ray energy spectra.

19. The method of claim 7, wherein the producing of the reduced number of image data sets comprises:
summing, based upon the plurality of projection measurement data sets, the reduced number of image data sets in a linearly weighted fashion such that image data is produced with attenuation values which correspond to differing polychromatic or monochromatic X-ray energy spectra.

* * * * *